(12) United States Patent
Novotny et al.

(10) Patent No.: US 11,206,980 B2
(45) Date of Patent: *Dec. 28, 2021

(54) PERSONAL WELLNESS MONITORING SYSTEM

(71) Applicants: Vlad Novotny, Los Gatos, CA (US); Michelle Novotny, San Jose, CA (US)

(72) Inventors: Vlad Novotny, Los Gatos, CA (US); Michelle Novotny, San Jose, CA (US)

( * ) Notice: Subject to any disclaimer, the term of this patent is extended or adjusted under 35 U.S.C. 154(b) by 492 days.

This patent is subject to a terminal disclaimer.

(21) Appl. No.: 16/369,576

(22) Filed: Mar. 29, 2019

(65) Prior Publication Data

US 2019/0282097 A1  Sep. 19, 2019

Related U.S. Application Data

(63) Continuation of application No. 14/741,695, filed on Jun. 17, 2015, now Pat. No. 10,249,214.

(Continued)

(51) Int. Cl.
| | |
|---|---|
| *A61B 5/00* | (2006.01) |
| *A61B 5/024* | (2006.01) |
| *G09B 19/00* | (2006.01) |
| *A61B 5/145* | (2006.01) |
| *A61B 5/11* | (2006.01) |

(Continued)

(52) U.S. Cl.
CPC ........ *A61B 5/0022* (2013.01); *A61B 5/02438* (2013.01); *A61B 5/1118* (2013.01); *A61B 5/14539* (2013.01); *G09B 19/0092* (2013.01); *G16H 20/60* (2018.01); *A61B 5/0059* (2013.01); *A61B 5/0205* (2013.01); *A61B 5/0537* (2013.01); *A61B 5/1112* (2013.01); *A61B 5/1123* (2013.01); *A61B 5/14532* (2013.01); *A61B 5/6898* (2013.01); *A61B 2562/0219* (2013.01); *G16H 10/60* (2018.01)

(58) Field of Classification Search
CPC . G06T 2207/10024; G06T 2207/30128; G06T 7/62; G09B 19/0092; G16H 10/60; G16H 20/30; G16H 20/60; G16H 30/40; G16H 40/63

See application file for complete search history.

(56) References Cited

U.S. PATENT DOCUMENTS

| | | | | |
|---|---|---|---|---|
| 2015/0168365 A1* | 6/2015 | Connor | ................... | G16H 20/60 356/51 |
| 2016/0012749 A1* | 1/2016 | Connor | .................... | A61B 5/00 600/13 |

* cited by examiner

*Primary Examiner* — Manuchehr Rahmjoo

(57) ABSTRACT

A complete personal nutrition, health, wellness and fitness monitor is disclosed that captures, monitors, and tracks many relevant health and wellness factors. Image of all consumed items is captured with a three dimensional reference object, matched to reference images in a database in terms of shape, color, size and texture, identified, and the volume of the respective items is determined. In addition, molecular optical fingerprinting of consumable products provides information about actual food composition, including vitamins and contaminants that affect food safety. Using energy and nutrition information of items in another database, full nutritional content and energy is evaluated for all of the items in the image. Combined with activity monitoring that captures energy output, the monitor actively tracks overall energy balance and nutritional content for every consumable item in real time, and makes proactive recommendations with respect to nutrition, exercise, and general lifestyle for overall nutrition, health, wellness, and fitness.

15 Claims, 14 Drawing Sheets

Related U.S. Application Data

(60) Provisional application No. 62/012,978, filed on Jun. 17, 2014.

(51) Int. Cl.
*G16H 20/60* (2018.01)
*A61B 5/0205* (2006.01)
*A61B 5/0537* (2021.01)
*G16H 10/60* (2018.01)

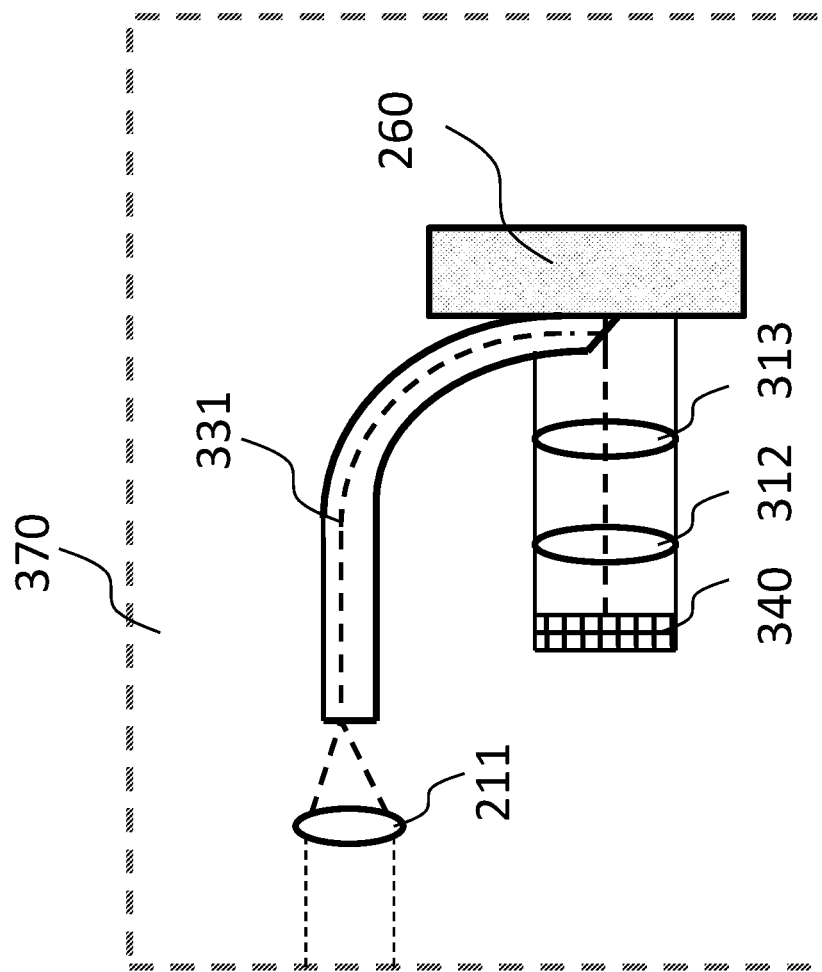

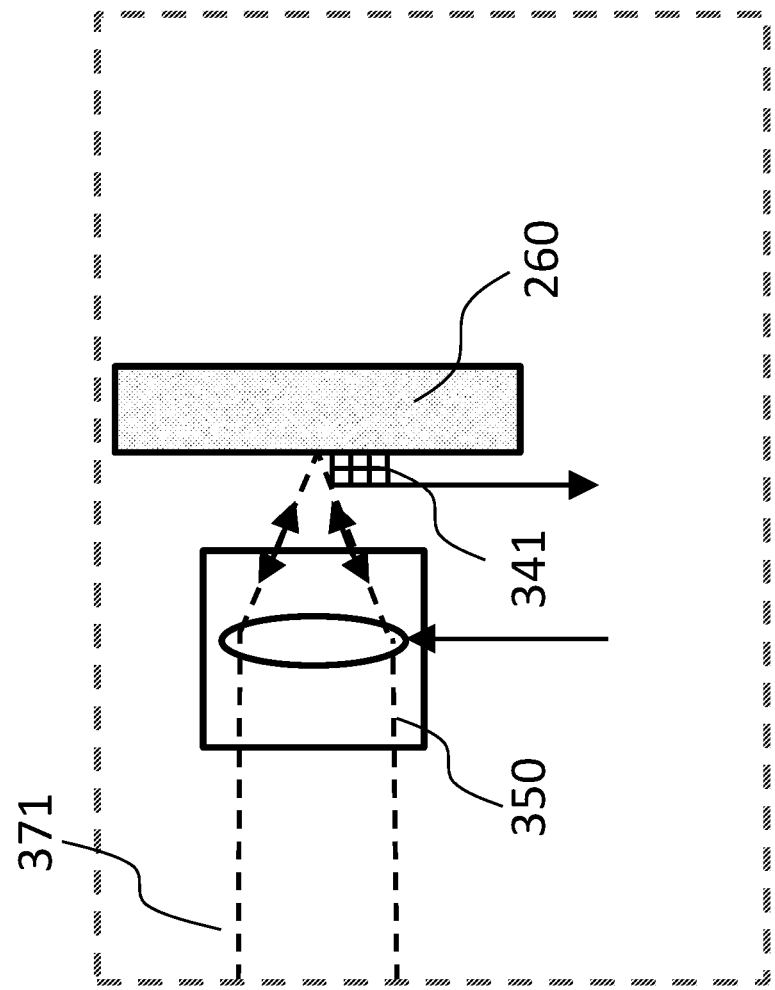

Top View

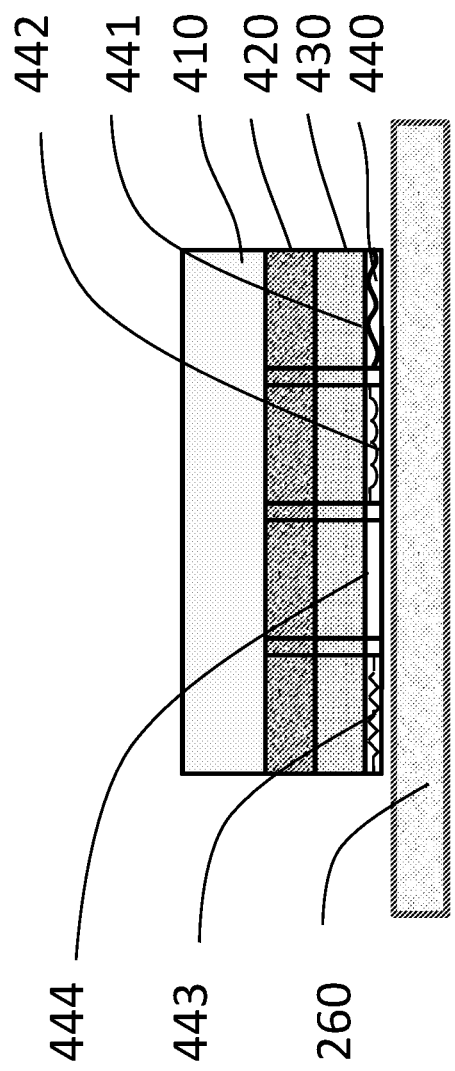

Top View

Side View

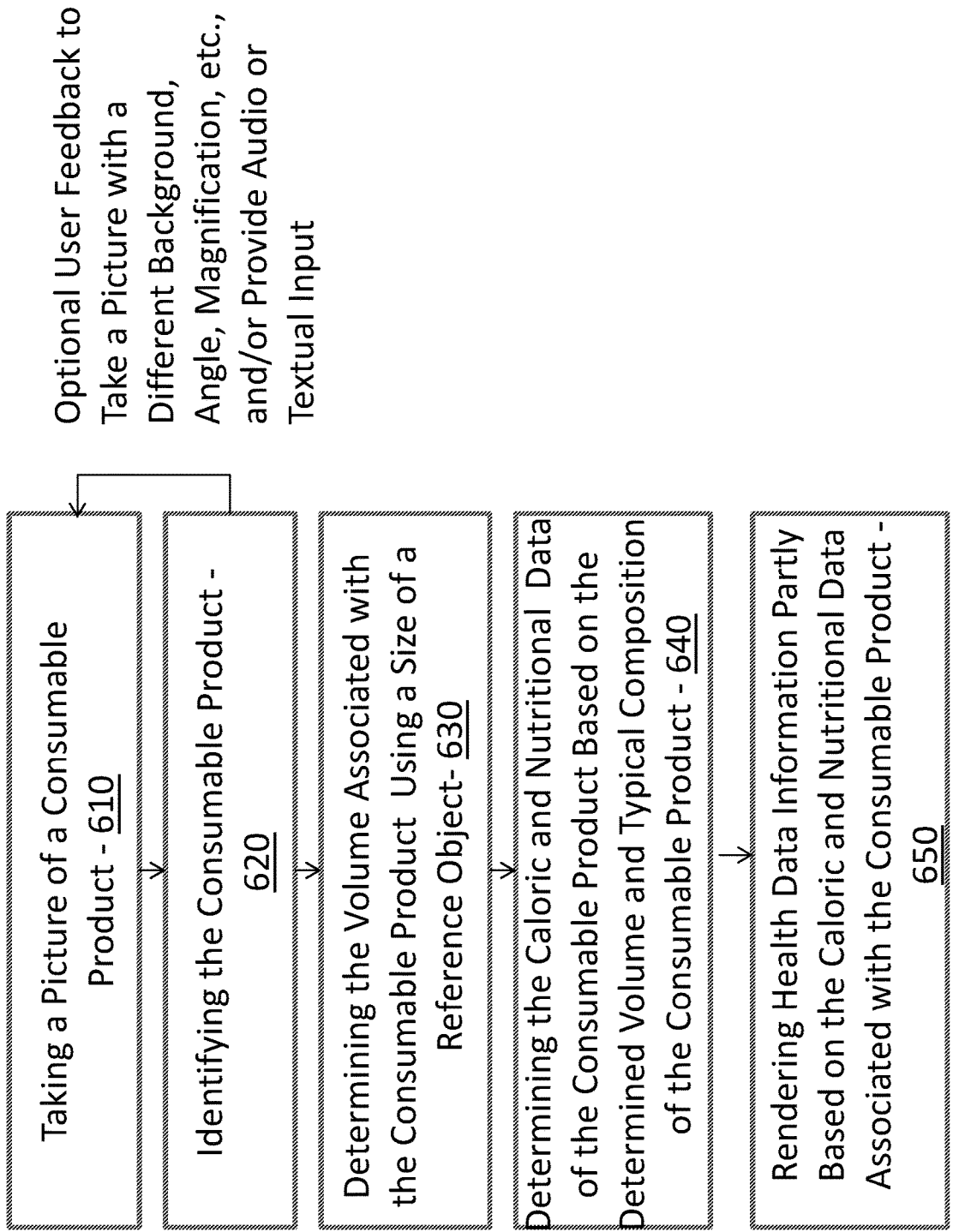

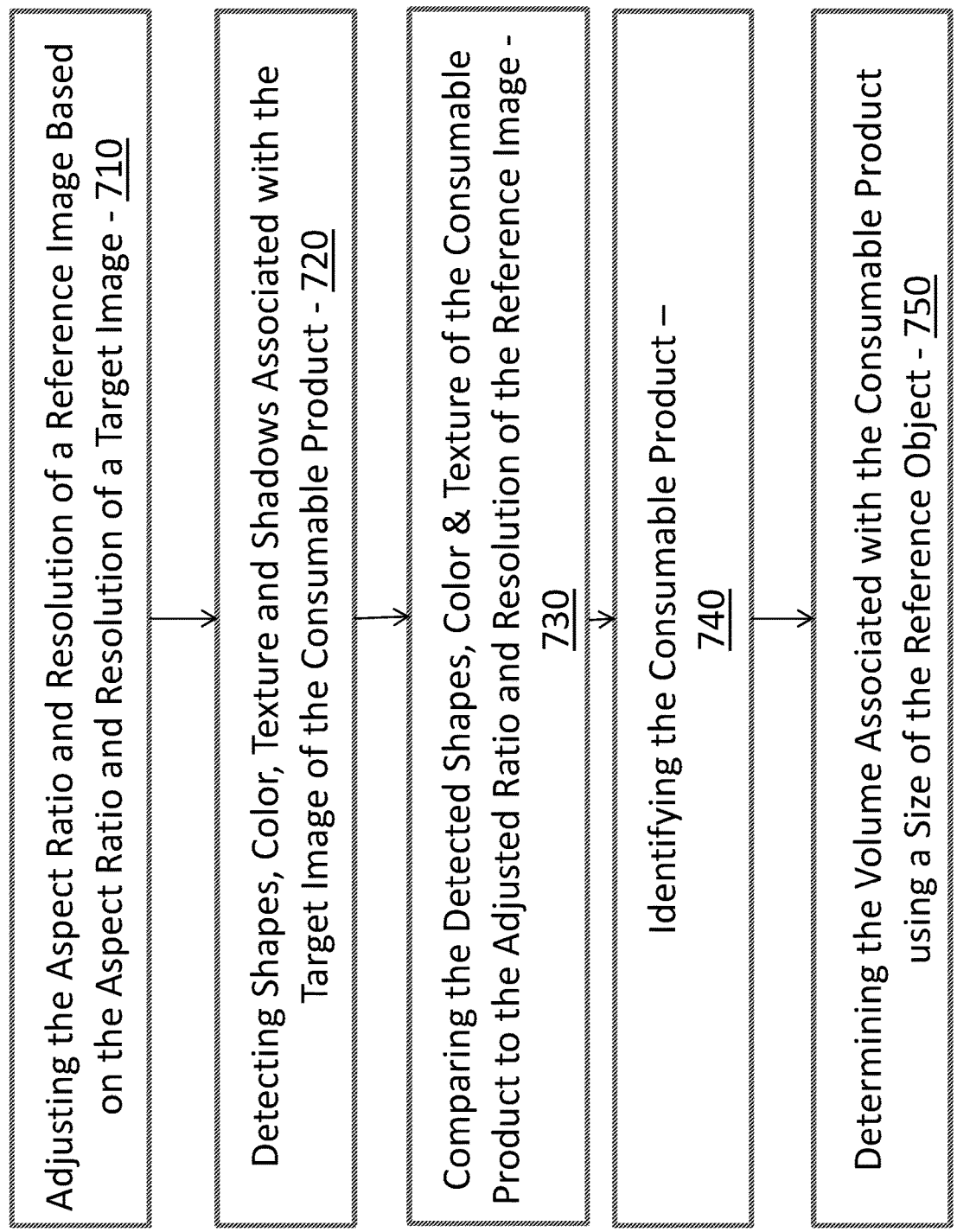

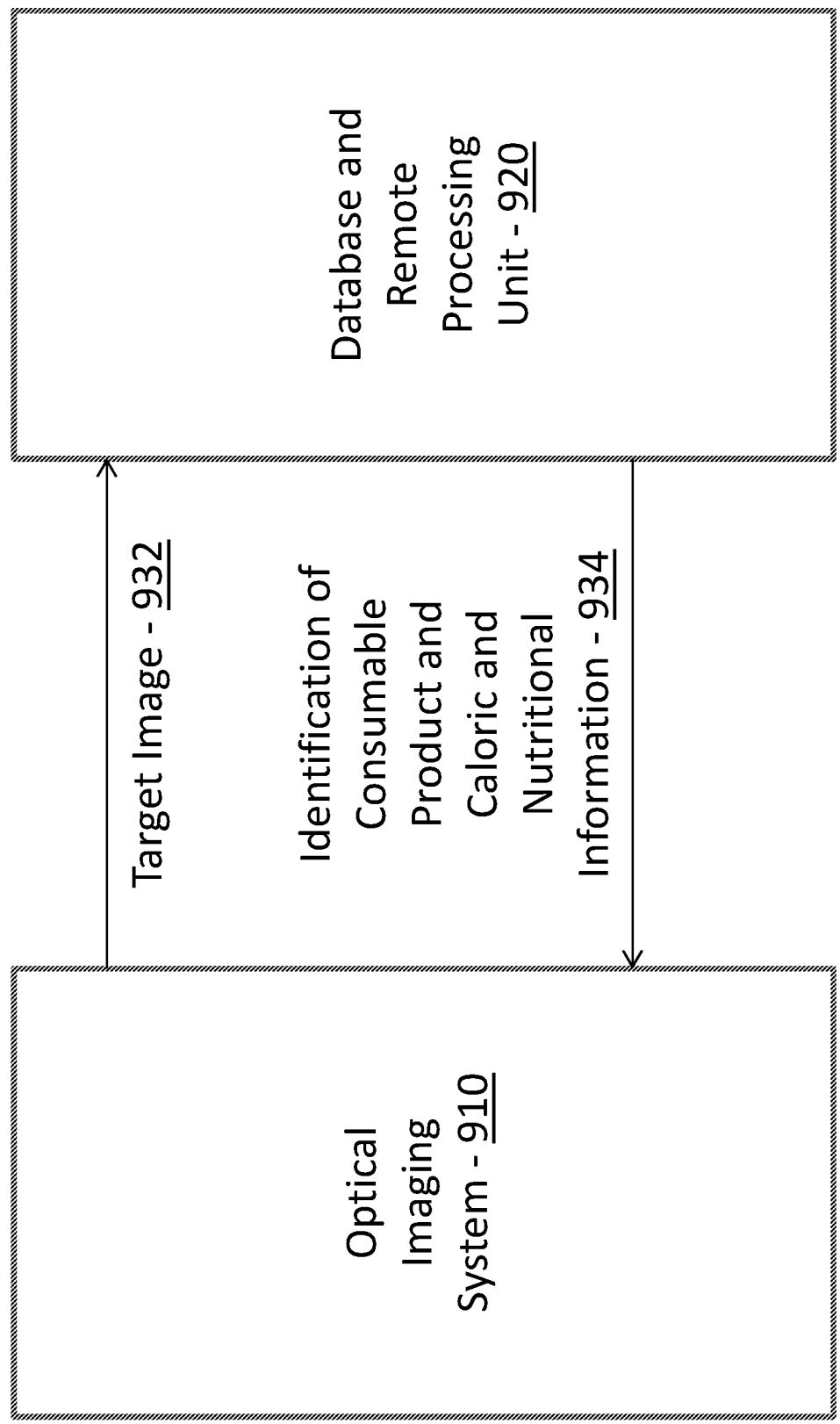

PERSONAL WELLNESS MONITORING SYSTEM

RELATED APPLICATIONS

This application claims the benefit of and priority to the provisional patent application No. 60/012,978, filed by V. Novotny, on Jun. 17, 2014, which is incorporated by reference herein in its entirety.

BACKGROUND

Personal nutrition, health, wellness, and fitness systems using electronic devices have become popular in recent years but they are relatively primitive at present. Many devices track the number of steps taken, number of stairs climbed, heart rate, level of oxygen in the blood, body temperature, respiration level, the supposed calories burned, etc. However, the tracked information is incomplete, providing very rough estimates for some characteristics and incorrect information for others such as calories burned.

SUMMARY

A need has arisen for a complete and mobile personal nutrition, health, wellness, and fitness monitor that will be able to capture, monitor, and track many relevant health and wellness factors, including but not limited to, food and liquid intake, composition of consumable products, vitamin and mineral content, physical activity, as well as other information such as heart rate, blood pressure, electrocardiogram ("EKG"), body fluids acidity and alkalinity quantified by pH, glucose level and oxidative stress level, among others. Based on these measurements, the monitor will actively track overall energy balance and nutritional content for every meal, every day, and will make proactive recommendations with respect to nutrition, exercise, and general lifestyle for improved nutrition, health, wellness, and fitness.

Complete personal nutrition, health, wellness, and fitness monitor ("Personal Monitor") based on image recognition, volume determination and molecular optical fingerprinting is disclosed. Image analysis of food and liquids to be consumed, including quantitative volume determination, is one of the health factors being monitored. Comprehensive information including complete nutritional content, as well as vitamin and mineral content and total energy input may be derived semi-quantitatively with image based analysis or quantitatively with molecular optical fingerprinting. These factors may be tracked, and, together with activity monitoring that follows energy spent (calories burned), energy balance may be derived and tracked, over any desired period of time. Proactive measures may be suggested to users in order to optimize caloric and nutritional input, along with activity and other recommendations.

BRIEF DESCRIPTION OF DRAWINGS

FIGS. 3A-3B illustrate a detection subsystem of a non-contact optical engine and a contact optical engine, respectively, in accordance with some embodiments.

FIGS. 4A-4B illustrate a sensor array with optical filters in top view and side view, respectively, in accordance with some embodiments.

FIG. 6 provides a schematic overview of methods of food and liquid identification, volume determination and caloric and nutritional analysis.

FIG. 7 outlines a method of determining the volumes of foods and liquids when the adjustment of image resolution and aspect ratio is required.

FIGS. 9A-9B outline methods for identifying consumable products and determining their caloric and nutritional content.

DETAILED DESCRIPTION

Figure 1:
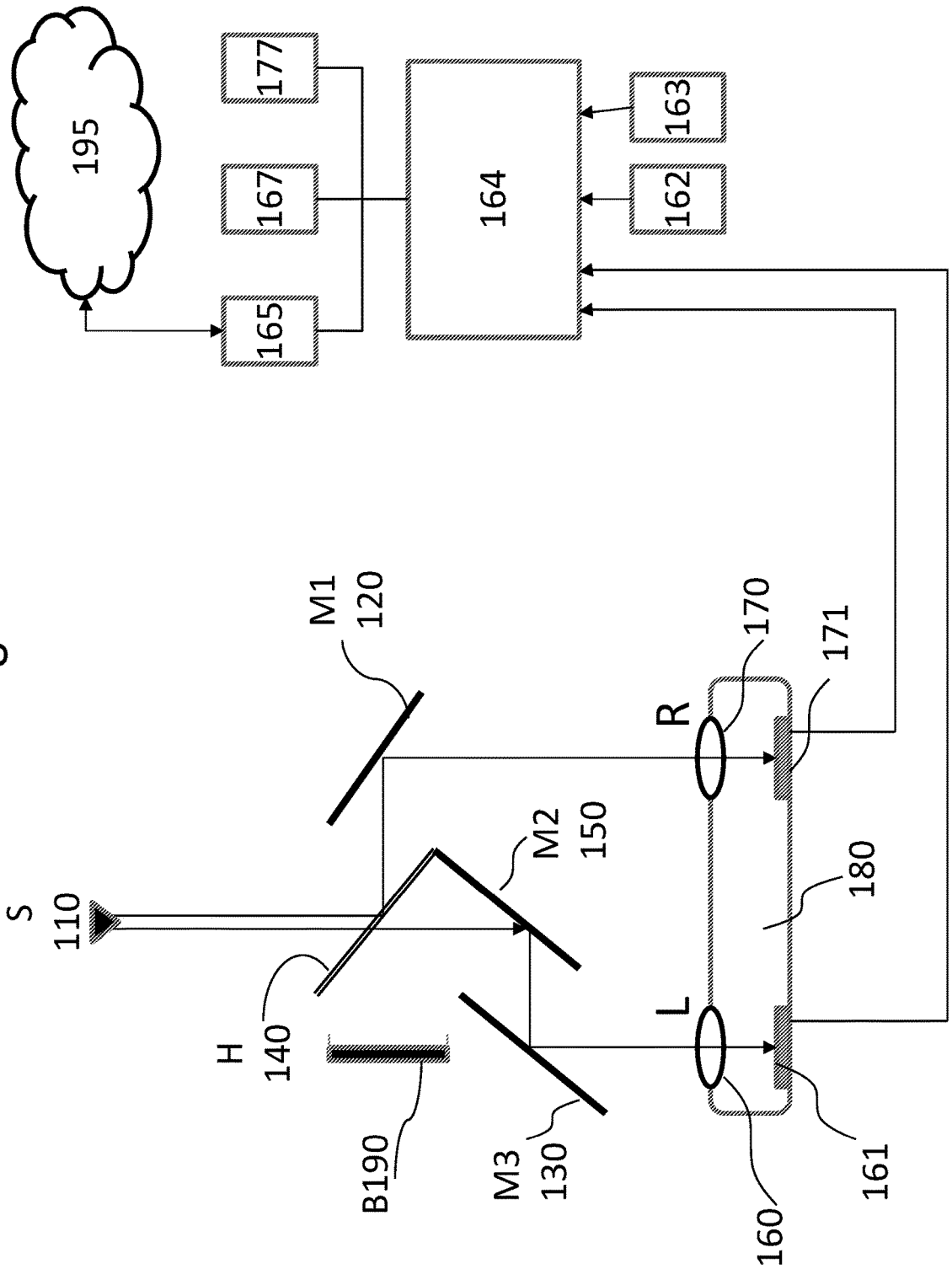
FIG. 1 illustrates an optical imaging system in accordance with some embodiments.

Reference will now be made in detail to various embodiments, examples of which are illustrated in the accompanying drawings. While the claimed embodiments will be described in conjunction with various embodiments, it will be understood that these various embodiments are not intended to limit the scope. On the contrary, the claimed embodiments are intended to cover alternatives, modifications, and equivalents, which may be included within the scope of the appended Claims. Furthermore, in the following detailed description, numerous specific details are set forth in order to provide a thorough understanding of the claimed embodiments. However, it will be evident to one of ordinary skill in the art that the claimed embodiments may be practiced without these specific details. In other instances, well known methods, procedures, components, and circuits are not described in detail so that aspects of the claimed embodiments are not obscured.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of operations or steps or instructions leading to a desired result. The operations or steps are those utilizing physical manipulations of physical quantities. Usually, although not necessarily, these quantities take the form of electrical, optical, or magnetic signals that are digitized and are capable of being stored, transferred, combined, compared, and otherwise manipulated in a computer system or computing device. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated or otherwise as apparent from the following discussions, it is appreciated that throughout the present disclosure, discussions utilizing terms such as "receiving," "converting," "transmitting," "storing," "determining," "sending," "querying," "providing," "accessing," "associating," "taking," "initiating," "identifying", "rendering," "modifying," "analyzing," "displaying," "processing," "adjusting," "detecting," "comparing," "matching," "generating," "shining," "using," or the like, refer to actions and processes of a computer system or similar electronic computing device or processor. The computer system or similar electronic computing device manipulates and transforms data represented as physical (electronic) quantities within the computer system memories, registers or other such information storage, transmission, or display devices.

It is appreciated that present systems and methods can be implemented in a variety of architectures and configurations. For example, present systems and methods can be implemented as part of a local computing system, a distributed computing environment, a cloud computing environment, a client server environment, etc. Embodiments described herein may be discussed in the general context of computer-executable instructions residing on some form of computer-readable storage medium, such as program modules, executed by one or more computers, computing devices, or other devices. By way of example, and not limitation, computer-readable storage media may comprise computer storage media and communication media. Generally, program modules include routines, programs, objects, components, data structures, etc., that perform particular tasks or implement particular abstract data types. The functionality of the program modules may be combined or distributed as desired in various embodiments.

Computer storage media can include volatile and non-volatile, removable and non-removable, media implemented in any method or technology for storage of information such as computer-readable instructions, data structures, program modules, or other data, that are non-transitory. Computer storage media can include, but are not limited to, random access memory (RAM), read only memory (ROM), electrically erasable programmable ROM (EEPROM), flash solid state memory, or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared, and other wireless media. Combinations of any of the above can also be included within the scope of computer-readable storage media.

A need has arisen for a complete and mobile personal nutrition, health, wellness, and fitness monitor that captures, monitors, and tracks many relevant health and wellness factors, including but not limited to, food and liquid intake, consumables composition, vitamin and mineral content, food and liquid contaminants such as pesticides and antibiotics, and physical activity, as well as other information such as heart rate, blood pressure, body temperature, respiration rate, oxygen level in blood, electrocardiogram ("EKG"), acidity and alkalinity level ("pH"), glucose level and oxidative stress level, among others. Based on these measurements, the monitor can then actively track overall energy balance and nutritional content for every meal, every day, and make proactive recommendations with respect to nutrition, exercise, and general lifestyle for improved nutrition, health, wellness, and fitness.

Energy balance requires a determination of energy input as well as energy output. Energy input consists of energy (caloric) content of, among others, proteins, carbohydrates, fats and sugars, consumed by an individual. Food and liquid content in relevant nutritional categories, including vitamin and mineral content, is required for comprehensive nutritional information.

When consumable products, including food, liquids, and supplements (individually, a "Consumable Product" and when one or more than one, "Consumable Product(s)"), are being monitored and associated detailed nutritional content is tracked, additional critical information may be obtained. Such information may include body hydration and mineral and vitamin levels essential for healthy body functioning. This comprehensive information may be compared with recommended daily values of Consumable Product(s), including vitamins and minerals, which are adjusted and scaled according to a users' personal parameters such as weight, height, sex and age. A system and device for mobile monitoring of nutrition, health, wellness, and fitness is disclosed here.

Referring now to FIG. 1, an optical imaging system in accordance with some embodiments is shown. The optical imaging system, as shown, is configured to identify information related to Consumable Product(s), e.g., food/liquid type, its components, volume of these components and approximate content of vitamins and minerals present. For example, the type of food may be fruits or vegetables such as apples or oranges, meats such as chicken or fish, and carbohydrates such as bread or pasta, etc.; the type of liquid may be soda, coffee, spirits, etc. Accordingly, from the composition of the Consumable Product(s), the caloric intake per given consumption step and its nutritional value are evaluated.

The optical imaging system in accordance with some embodiments, including mirrors M1 120, M2 150, and M3 130, half silvered mirror H 140, a stereo camera 180 with left camera including optical lenses L 160 and imaging array 161 and right camera including optical lenses R 170 and imaging array 171, a processing unit 164, an optional audio input component 162, an optional textual input component 163, a transmitter 165, a display 167, and an audio output 177. The transmitter 165 may be coupled to a cloud 195.

It is appreciated that the particular configuration of the mirrors, cameras, and image arrays as shown in FIG. 1 is for illustrative purposes and not intended to limit the scope. For example, one lens system and one imaging array may be used for non-stereo, two dimensional ("2D") imaging. In other stereo, three dimensional ("3D") embodiments, multiple mirrors with or without lenses and two cameras may be used. According to some embodiments, one large composite lens and stereo camera may be used. In one illustrative example, systems with mirrors or prisms and stereo camera may be used. Other exemplary configurations may include systems with two cameras.

Images of various Consumable Product(s) are the universal inputs, regardless of what is being consumed, whether from restaurants or fast food establishments (collectively, "Restaurants"), pre-packaged meals, meals prepared from scratch, snacks, fruits, vegetables, drinks, etc. In the case of Restaurants, nutritional content is increasingly becoming available such that the nutritional content can be inputted automatically from the Restaurants' respective websites or via manual input by the user, e.g., through the optional audio input component 162 or optional textual input component 163. Even in these cases, however, in order to independently verify the nutritional content, images are taken in order to account for the volume of the Consumable Product(s). Volume information is also useful in situations where the information is not available otherwise, e.g., website, etc.

In order to determine the caloric intake, a picture of the Consumable Product(s), e.g., food, liquid, etc., is taken. The taken picture is referred to as a target picture throughout this application. The target picture may be a 2D or 3D image that may contain a standard calibration feature. A picture may be taken at any angle, e.g., perpendicular or side angle.

For a more accurate determination of the volumes of Consumable Product(s), a known 3D object or a reference may be used. For example, an object with known shape and dimensions in all three (x, y and z) directions (referred to here as the "Reference Object") may be included beside the Consumable Product(s) when the picture is being taken. The Reference Object may be any object with known dimensions, e.g., a credit card, a wallet, a currency coin, a stack of coins, a die, a chap stick tube, a golf ball, etc. The dimensions of the Reference Object are generally known or may be provided by the user, e.g., via optional audio input component 162, optional textual input component 163, etc. The Reference Object may be used to obtain optical magnification when taking the image and to correct for variability in the tip and tilt angles of the target picture. Quantitative volumetric data may be indeterminable unless the optical magnification is known when each picture is taken. The known dimensions and shape of the Reference Object are used to determine the optical magnification and, therefore, the volume of the Consumable Product(s) when the picture is being taken. Determination of volumetric information via the Reference Object is described further below.

The stereo camera 180, according to some embodiments, has imaging arrays 161 and 171 with synchronized functionality such that two pictures may be captured at the same time. In other words, two pictures are taken simultaneously, one by the imaging arrays 161 and one by the imaging arrays 171. Since two pictures are taken simultaneously by the imaging arrays 161 and 171, the optical magnification of the two captured pictures remains the same and the viewing angles remain substantially the same with only slight differences between the two due to the positions of the two lenses 160 and 170 and imaging arrays 161 and 171. According to an illustrative embodiment, the light S 110 from the object, e.g., Consumable Product with the Reference Object may be brought onto the half silvered mirror H 140. In some embodiments, 50% of light may be reflected to the mirror M1 120 and directed to the right optical lens system 170 of the stereo camera 180. The remaining 50% of light may be transmitted through the half silvered mirror H 140, directed onto the mirrors M2 150 and M3 130 and onto the left optical lens system 160 of the stereo camera 180.

In one embodiment, the optical imaging system may include a light trap B 190 to absorb any unwanted scattered light that would degrade the images. The left and right images may be captured by imaging arrays 161 and 171, respectively, such as Complementary Metal Oxide Semiconductor (CMOS) or Charged Coupled Device (CCD) type arrays.

The digital data associated with the target picture may be transmitted to the processing unit 164. The processing unit 164 may be part of a smart mobile device such as phone, tablet or mobile computer. In some embodiments, the processing unit 164 may receive inputs through other components, e.g., the optional audio input 162 and the optional text input 163.

The processed data may be rendered on the display 167 or output through other means, e.g., audio output 177. In some embodiments, the processed data may be transmitted via its transmitter 165 to other devices for further processing or rendering, and the rendering component may be a display, an audio output, etc. It is appreciated that in some embodiments, the raw data may be transmitted to an external device for processing and subsequently the processed information may be received by the system for further processing and/or rendition.

The processing of the target picture in order to determine the specific Consumable Product(s) and its volume and then its caloric input is now described. In some embodiments, an image of the Stock Keeping Unit (SKU) may be used to identify the Consumable Product, and its volume, components, and weights. In other embodiments, an image of the Consumable Product(s) may be used, the product identified and its volume determined using various image processing methods.

Cloud 195 may include various databases, including a database that stores reference images (individually, a "Reference Image" and collectively, the "Reference Images") and typical nutritional content of Consumable Products, including amounts of vitamins and minerals. Each Reference Image may be previously taken with a high-resolution camera. As a result, the Reference Image may have a higher resolution and possibly a different aspect ratio than the target picture. In order to match the resolution and aspect ratio of the Reference Image and the target picture so that a direct subtraction of images, if necessary pixel by pixel, can be performed, the resolution and aspect ratio of the Reference Image may be adjusted as needed, e.g., decreased, increased, etc., to match the resolution and aspect ratio of the target picture. Image recognition may be performed on the target picture in order to match the target picture to a Reference Image. Image matching may use the corrected and scaled target picture to identify the corresponding Reference Image, by matching shape, color, size, and texture. Edge detection may be used to enhance the matching of the target picture to the Reference Image, which is described further below.

A single, 2D picture does not have third dimension information directly. Many different approaches may be used to determine the third dimension. In one embodiment, the third dimension is approximated based on typical volumetric shapes and sizes of individual items in the database of Reference Images. The database contains both the Reference Images and the ratios of the three dimensions (x/z and y/z) of each Reference Image. Once the 2D Consumable Product(s) has been identified using image matching of the Consumable Product image with the Reference Image in the database, taking into account edge detection, shape, color, and texture matching, the Reference Image may be used to determine the third dimension of the 2D Consumable Product(s) by expressions $$z_t = z_r \cdot (x_t/x_r) \text{ and } z_t = z_r \cdot (y_t/y_r)$$

where $x_r$, $y_r$, and $z_r$ are dimensions of the Reference Images and $x_t$, $y_t$ and $z_t$ are dimensions of the Consumable Product(s). In other words, the edge detection, shape, color, and texture matching may be performed between the target image and the Reference Image(s) in order to identify the Consumable Product. In some embodiments, the third dimension of the Reference Image(s) and the optical magnification and aspect ratio of the target image and the Reference Image(s) may be used to determine the third dimension of the Consumable Product(s).

In some embodiments, the shadows that may appear in the target picture may be exploited in order to provide third dimension information. Shadows complicate edge detection and create regions with apparent differences even when the features are uniform. However, the Reference Object in the target picture casts a predictable shadow when the Reference Object is 3D. The shadow associated with the Reference Object may be used to identify other shadows, calculate the height of items casting shadows, and improve edge detection.

According to some embodiments, spurious edges created by shadows are detected, removed from the target picture, and the areas covered by shadows are brought to the background. If any shadows cover another item in the target picture, the shadows may be corrected to reflect the accurate light intensity and color of the shadowed item. As such, shadows may be removed by inserting a background where the shadows were.

In order to identify the type of Consumable Product, the shape enclosed by each contiguous edge may be determined, e.g., square, rectangle, circle, ellipse, triangle, parallelogram, etc. Each item with an enclosed edge pattern may be categorized by the shape that most closely fits the Consumable Product. In some embodiments, three primary color coordinates may be used by averaging blue, green, and red subpixels within the Consumable Product to determine the color. In some embodiments, two color coordinates defining the color of each Consumable Product using the CIE (International Commission on Illumination) color triangle are derived. If the color is very nonuniform within the boundary of each Consumable Product, then the Consumable Product may be split into sub-items and each sub-item may be represented by color subpixels averages or color triangle coordinates and assigned texture values. The texture may be characterized by light intensity variations and spatial dimensions of regions having such intensity variations within contiguous boundaries.

Once the shape, size, color, and texture categorization is completed, a comparison of the target image to the Reference Image(s) is performed in order to find a match. Once a match is found, the quality of the match may be evaluated. The quality may be expressed by the Confidence Level ("CL"). The CL may be related to the sum of scaled differences between the Reference Image and target picture sub-pixel values, divided by the sum of sub-pixel values. If the confidence level of the identification is high and/or a SKU image is used, then the volume may be determined and additional nutritional information of the identified item(s) may be obtained. If the confidence level is not high enough due to factors such as illumination differences causing color shifts between the target picture and the Reference Image, then the user may be prompted to provide assistance to specify the Consumable Product either using audio input component 162 or textual input component 163 or via any other input methods. In some embodiments, a second attempt may be made to perform the shape, color, size, and texture matching, and a new confidence level may be calculated. If the new confidence level is still inadequate, the target image may not undergo further processing, but it may be tracked for corrective measures based on artificial intelligence for future analysis.

If the confidence level is satisfactory, the Consumable Product is identified and the data analysis proceeds, e.g., to determine its volumetric information. If the target picture is a single 2D image, then a 3D equivalent shape, e.g., cube, rectangular box, sphere, cone, cylindrical plate, etc., may be assigned to the Consumable Product. Volumetric information may be determined using the cast shadows. The illumination beams are either collimated (sun light) or nearly parallel because the light source is typically far away from the target picture. If the picture is taken with flash (i.e. the light source is at the same distance from the target picture as the camera optical system), then the light propagation geometry may be known and shadows can be projected. The heights of the unknown items $H_j$ are given by equation:

$$H_j = L_j (H_r / L_r)$$

where $L_j$ are the lengths of the shadow of the Consumable Product and $H_r$ and $L_r$ are the height and the shadow length, respectively, of the Reference Object. As such, the edges of the target picture and the Consumable Product may be determined along with its volume.

In some embodiments, volumetric information may be obtained using several target pictures that include a Reference Object, e.g., two pictures with different viewing angles, or by capturing one target image that is three dimensional with a Reference Object. It is appreciated that the 3D image may be taken using an optical imaging system that has two separate cameras, or by capturing a video of the Consumable Product(s) with a Reference Object in which the viewing angle of the video camera is deliberately changed, or by using a holographic camera. As described above, the shadows can be exploited to improve height analysis.

For pre-packaged Consumable Product(s), the target picture may be captured by taking a photo or video image of the SKU. In some embodiments, the bar code may be converted into a digital representation by optical pattern recognition ("OCR") of the SKU number, and the portion size may be input through optional audio input component 162 or through optional textual input component 163 or via any other input methods. As the identification of a large variety of Consumable Product(s) is challenging, the user can provide optional information at any time through various inputs into the device. For example, the user may provide a list of ingredients with respective weights and/or volumes for Consumable Product(s) prepared at home, from data obtained from external sources such as a wireless or wired balance/scale that transfers data directly into the mobile device.

The SKU often contains valuable information such as quantitative nutritional information, which permits more accurate accounting of the Consumable Product(s). The quantitative nutritional information available in the SKU database may include: total fats with a break-out of saturated fats and trans fats, total carbohydrates and the portions of dietary fiber and sugars, proteins, cholesterol level, the amount of sodium, potassium, calcium, iron and other minerals, and vitamin content for common vitamins, including A, B, C, etc., to name a few.

The target picture may be tagged, whether it is a SKU or a Consumable Product with or without a Reference Object, with a time and date stamp in order to facilitate chronological tracking. Depending on the complexity of the target picture, the image processing may be performed locally, e.g., by the device itself, or performed by a device external to the optical imaging system, e.g., transmitted to an external processing unit for processing.

Complex backgrounds may complicate the image processing of the Consumable Product. In some embodiments, voice and/or text reminders may be provided to the user to request a different background when taking the target picture if it is determined that the background appears too complex and may result in inaccurate results. In some embodiments, the device may prompt the user to retake the picture and/or video with a different background if the accuracy of the image processing is below a certain threshold deemed unacceptable.

In some embodiments, once the Consumable Product is determined along with its volume, the energy analysis starts. The associated energy and nutritional content (that parallels the type of information in the SKU database) of each Consumable Product may be available from a database. This database may be used to calculate the energy in, nutrition value, vitamin content, and mineral content of each Consumable Product.

The basic algorithm to determine consumed energy E is given by the equation $$E = \Sigma(\rho_i \cdot V_i \cdot e_i)$$

where the sum is over all components i and $\rho_i$, $V_i$, and $e_i$ are the density, volume and energy density, respectively, of each Consumable Product. Other categories of nutritional information are handled in a similar manner to complete the overall calculation. The resulting information consists of total energy in, complete breakdown of nutritional content in all nutritional categories, and quantitative amounts of all vitamins and minerals.

The resulting data may be displayed before consumption so that the user can make an informed decision (i.e., to consume, make volume/quantity or other adjustments, or not consume). The data associated with current consumption or cumulative data for a full day of consumption may be presented and displayed with historical data for efficient tracking. Based on the user's personal data, including weight, height, sex, age, etc., feedback and recommendations may be provided, including hydration levels and corresponding recommendations thereto.

Learning algorithms that leverage artificial intelligence may be used to simplify the image processing and analysis for repeat Consumable Product(s) especially since many users consume similar or identical items over time. By checking for uniqueness and repeatability, repeat Consumable Product(s) may be captured, thereby reducing processing power requirements and improving accuracy of results. The content and nutritional information results may complement additional health and wellness data to improve the user's experience by providing a more complete picture of the user's overall nutrition, health, wellness, and fitness. Examples of additional health and wellness data may include, but is not limited to, heart rate data, oxygen level in the blood, EKG information, systolic and diastolic blood pressure, respiration rate, body temperature, blood glucose level, pH values, oxidative stress levels, etc. This data may be available from other monitors, systems, and/or applications embedded in the mobile device or in companion devices with wireless or wired connectivity to the mobile device.

It is well known that pH measures the acidic or alkaline nature of a body's tissues and fluids. The pH scale is logarithmic and ranges from 0 to 14, where 0 is very acidic, 7.0 is neutral, and 14.0 is very alkaline. Acids are naturally corrosive and inflammatory, and they irritate the internal organs they come in contact with. Too much acid also contributes to the demineralization of bones, teeth, and joints, and negatively impacts urinary and gastro-intestinal tracts. Low pH results in low energy, poor digestion, difficulties in losing weight, aches and pains, and other, more serious health disorders. An acidic environment also provides a breeding ground for microbes, which can compromise one's health.

The human body should be slightly alkaline, around 7.4, with blood in a very narrow range of 7.37 to 7.45. Given the inconvenience in measuring blood pH directly, urine and/or saliva pH measurements are good substitutes. The pH of urine can range anywhere from 4.5 to 8.5 and may ideally be around 6.75. Saliva pH can range from 4.5 to 7.5 and may preferably be in the 7.0 to 7.5 range.

A pH level may be measured using a strip loaded with a reagent that changes color according to the pH of the fluid applied to it. A single reagent or multiple reagents for higher accuracy can be used in single or multiple strip configurations. By visually comparing the color of a testing strip with a standard color chart, pH may be evaluated, albeit crudely. Precise color measurements are possible if the color is measured spectrophotometrically. An adequate substitute for spectrophotometry may be accomplished by taking an image of a testing strip and reference color chart using a 2D version of the FIG. 1 optical imaging system. A color imaging analysis as described above may be performed to determine the color of the strip, removing the subjectivity of a person's visual comparison, and, consequently, the pH level. A reference color chart is preferably set beside the test strip for direct color matching. The color chart may be stored in the database of Reference Images so that it can be used when the test strip image does not include the color chart. The results of pH measurements are stored together with a date and time stamp and are handled in a similar fashion as Consumable Product(s). Specific nutritional and liquid intake recommendations to achieve an optimum pH level are provided based on the difference between the measured and optimum pH levels.

Energy usage or consumption is based on overall activity. Energy usage includes energy spent during physical activities associated with movement, e.g., walking/running/hiking, dedicated exercise, etc., and energy spent during periods of background activities, e.g., sleeping, sitting/standing, breathing, etc. Energy consumption takes into account the differences between body temperature versus outside temperature, as well as respiration rate, heart rate, blood oxygen level, perspiration rate and other factors obtained from other monitors, systems, and/or applications. These background activities are combined with physical activities in order to arrive at a user's complete energy spent on an activity-by-activity basis as well as on a daily basis.

It is appreciated that according to some embodiments, the energy spent in physical activities may be measured using various methods. For example, an accelerator, a gyroscope, pressure sensors detecting elevation differences, Global Positioning Sensor ("GPS"), etc., may be used. The distance traveled and the velocity of motion can also be derived from GPS information and time recorded for specific activity. The kinetic and potential energies spent may be calculated using velocity, mass and time of physical activities, and elevation differences.

The accuracy of caloric intake determinations can be increased by using typical compositions of identified items, and, further, by monitoring Consumable Product content data. By using molecular optical fingerprinting as described below in FIGS. 2-5, Consumable Product content data can be more accurately and quantitatively captured. In addition, to specifically monitor food safety, including determining the presence and concentrations of possible contaminants, such as pesticides, antibiotics and other undesirable or dangerous additives, molecular optical fingerprinting may be used. When molecular optical fingerprinting is included in the system, invaluable, comprehensive Consumable Product(s) safety information may be obtained in addition to the quantitative data of Consumable Product composition and concentration of vitamins.

The operational principle underlying non-invasive molecular optical fingerprinting of specific chemical and/or biological species relies on quantitative measurements of optical absorption or Raman spectra caused by these species as a function of spatial position in three dimensions, i.e. as a function of x, y and z where z is in the direction perpendicular to the surface of the Consumable Product(s).

To obtain accurate concentrations of specific chemical and/or biological species in inhomogeneous and highly scattered matrices that Consumable Product(s) represent, multiple spectral measurements may need to be performed using different optical paths. The embodiments described below eliminate or significantly reduce specular and diffuse scattering from the surface of the Consumable Product and enable the acquisition of optical absorbance or Raman spectra for multiple optical paths, thus providing the concentration of chemical and/or biological species of interest.

The chemical and/or biological species of interest are often present at very low concentrations in the presence of high levels of strong scatterers and high concentrations of other absorbing species or vibrational chemical groups that have significant or dominant optical responses in the infrared or Raman spectra. At the same time, it is often useful to acquire this spectral and spatial optical absorbance data in short time scales, in effect capturing the spectral dynamics of these species. It is desirable to acquire data in multiple dimensions—three spatial dimensions x, y, and z, and wavelength.

The optical engine architectures for infrared and Raman spectroscopy outlined below enable data to be acquired with multiple optical paths simultaneously and high signal collection efficiency while eliminating background signals without mechanical or optical scanning.

Optical engine architectures according to the embodiments described herein include one or more stationary illumination beams and an optical detector array (called simply a detector array below) that may be in contact with the Consumable Product (contact between the detector surface and the Consumable Product surface occurs when the distance between the detector surface or its window and the Consumable Product surface is about equal to or less than the size of the optical detector elements or their pitch). In some embodiments, the detector array or illumination element may be within close proximity to the surface of the Consumable Product which is often rough and inhomogeneous optically.

Optical background signals may overwhelm the relevant signals of interest making it challenging to separate them when sample surfaces generate large, specularly reflected and diffusely scattered signals that are distributed over a full half solid angle. In the disclosed embodiments, no spatial scanning is required; instead, optical data may be acquired simultaneously in parallel from many detection channels, yielding data for multiple optical paths with variable depth and surface positions.

Figure 2:
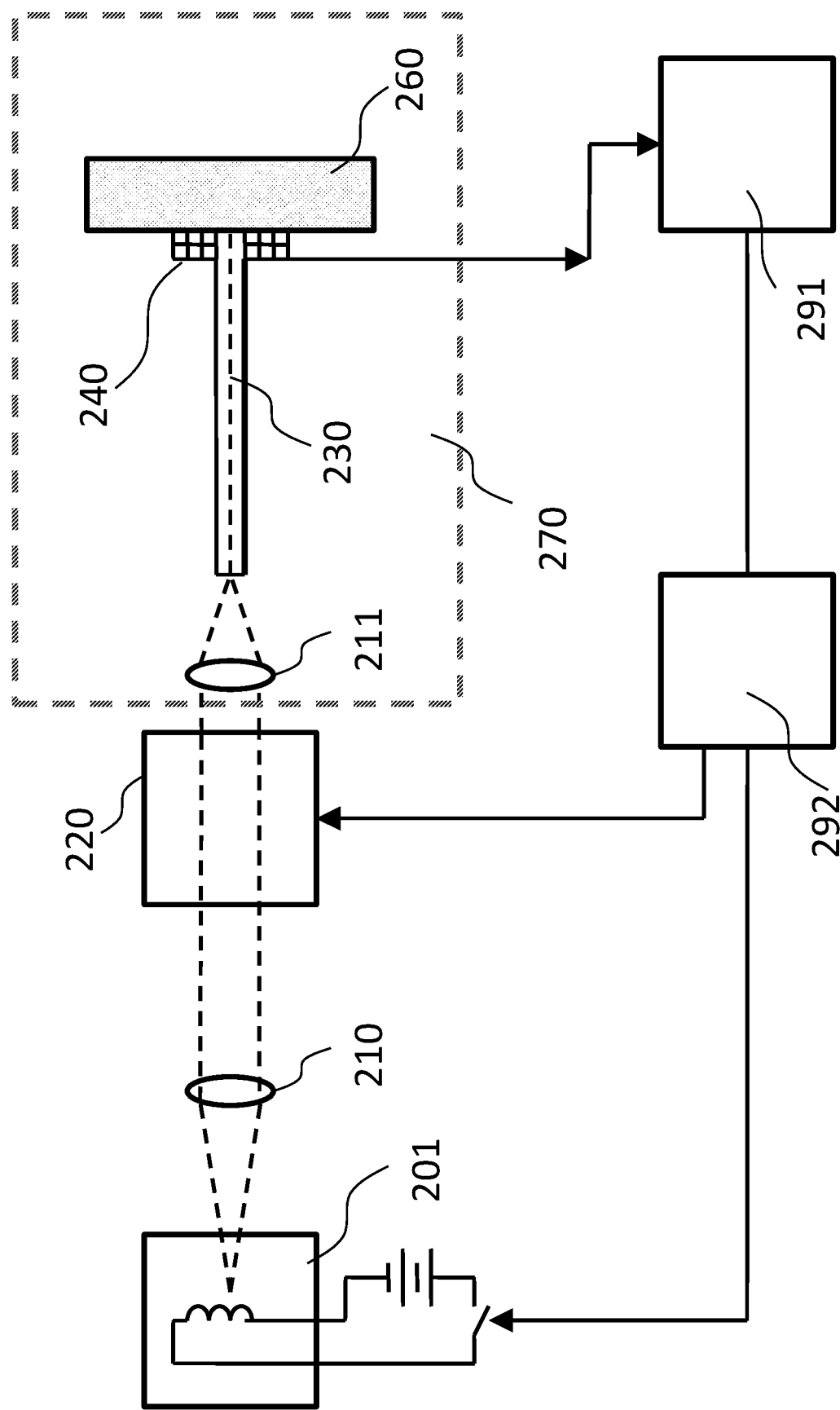
FIG. 2 illustrates a contact optical engine architecture in accordance with some embodiments.
Figure 4A:
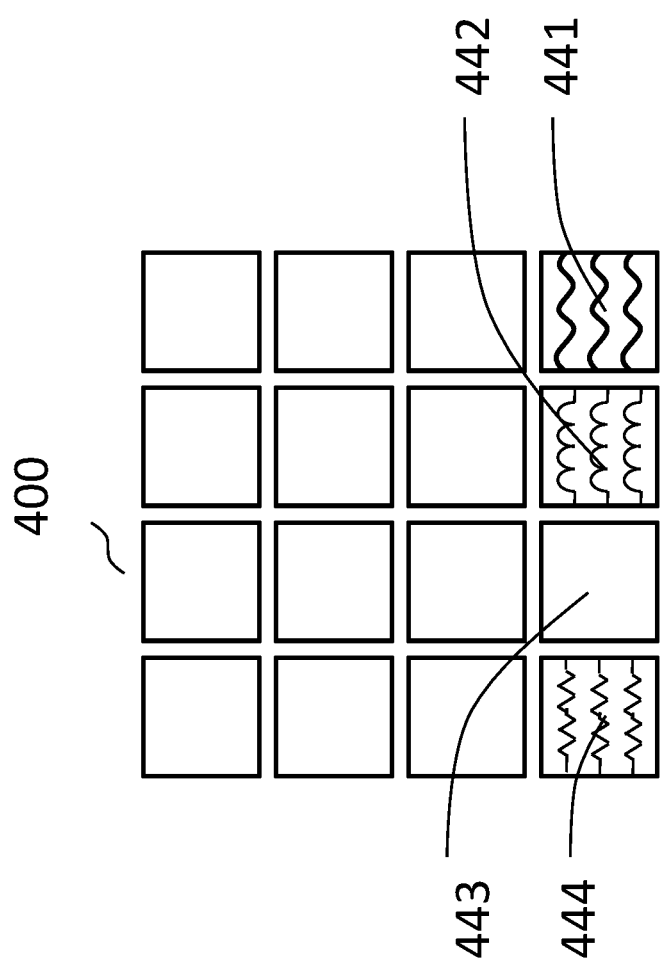

The optical engines for molecular optical fingerprinting have three basic elements, as shown in FIG. 2—light source 201, optical interferometer 220, and detector array 240. In FIG. 2, fiber 230 (which provides illumination in the center of the detector array 240) and the detector array 240 are in contact with the Consumable Product 260. The light generated by light source 201 is collimated with optical component 210 and directed onto the entrance opening of the optical interferometer 220. The light from the optical interferometer 220 is coupled by optical components 211 into the fiber 230 that brings the light to the surface or subsurface of the Consumable Product 260. The diffusely scattered optical signals from the Consumable Product 260 are captured by the detector array 240. Collectively, optical components 211, fiber 230, detector array 240, and Consumable Product 260 make up the assembly 270. The electrical digital signals from the detector array are amplified and digitized, fed into the data acquisition system 291, and then into the controller and signal processor 292. Optical absorption peaks and/or Raman peaks and their intensities for the multiple optical paths determine the presence and concentration of species/components of interest in the Consumable Product.

One type of light source 201 may be a blackbody radiation light source that has broad wavelength output with illumination ranging between 200 nm and 10000 nm, depending on the temperature of the tungsten filament. Another light source 201 may be Light Emitting Diodes (LED), lasers, tunable lasers or lasers in combination with several phosphorescent materials that may be combined at various proportions to provide high, desired phosphorescent light intensities in the most relevant spectral regions. The selection of light sources is based on a variety of factors, including the spectral range that needs to be covered, as well as the required sensitivity, power consumption, and size and cost of the system. If a monochromatic light source with very narrow wavelength broadening is required for vibrational spectroscopy, such as Raman spectroscopy, solid state laser diodes may be the appropriate light sources. The optical interferometer 220, that enables acquisition of the spectra, may be Michelson type with beamsplitter, movable mirror and stationary mirror, or integrated fiber optic Mach-Zender type, or Rippel Jaacks type, etc. For mobile applications, a small optical interferometer with low power consumption and insensitivity to tip and tilt changes, e.g., Rippel Jaacks, is desirable. The moving optical interferometer components can be driven by a small, low power electrostatic or electromagnetic actuator built using Micro Electro Mechanical Systems (MEMS) or voice coils.

According to some embodiments, the background specularly reflected and diffusely scattered light from the Consumable Product 260 surface is neither collected nor detected by the detector array 240. In addition, with the center illumination with respect to the symmetrically distributed detector array 240 around the illumination beam, most of the light in the half solid volume can be collected with the large size detector array 240. The configuration described here provides significant advantage over other optical architectures since the maximum collection efficiency (close to 100% of the half solid volume, i.e. half sphere solid angle of $2\pi$) may be achieved while interfering background signal is not collected.

The architecture in FIG. 2 normally includes an optical window to separate the detector array 240 from the Consumable Product 260, especially when the Consumable Products are food and/or liquids that contain various particulates and contaminants (without an optical window, the sensitive detector array surfaces can be contaminated or damaged by electrostatic discharge). The optical window can be easily cleaned if contaminated, but it should be segmented in order to avoid optical cross talk, as described below.

For detection in infrared region from about 800 nm to 2500 nm, the detector array 240 can be based on InGaAs materials with or without extended range, PbS, PbSe or HgCdTe materials, or microbolometers that have very broad spectral responses. When acquiring ultraviolet, visible and near infrared (up to 1000 nm) spectra, the detector array 240 may be silicon photodiode based.

The signals from the individual detectors that make up the detector array 240 may be amplified and digitized with analog-to-digital converters incorporated into the Read Out Integrated Circuit (ROIC) that may be fabricated under the detector array 240. The electrical digital signals may be fed into the data acquisition system 291 and then into the controller and signal processor 292. The controller and signal processor 292 synchronize the operation of the optical engine components, in particular, turning the light source 201 on and off, operating the optical interferometer 220, and collecting digitized data from the ROIC under the detector array 240.

The electrical digital signals may be analyzed with the controller and signal processor 292, including Fourier Transform computation, averaging, scaling and storing spectral data. The maximum acquisition and processing efficiency may be achieved with these architectures as all spectral data are collected and processed in parallel. Capturing time dependent phenomena may be limited by the scanning frequencies of the optical interferometer 220. When the optical interferometer is based on MEMS, high scanning resonance frequencies can be obtained, resulting in very short scanning and acquisition times.

One detection subsystem of the FIG. 2 optical engine architecture is shown in FIG. 3A where the elements in the assembly 270 of FIG. 2 are substituted by the elements in the assembly 370 in FIG. 3A (except for the optical components 211 which are the same in FIGS. 2 and 3A). The placement of the detector array differs between the embodiments described in FIG. 2 and that described in FIG. 3A. More specifically, the detector array 240 in FIG. 2 may be in contact with the Consumable Product 260 surface while the detector array 340 in FIG. 3A may be positioned at a distance away from the Consumable Product 260 surface. The detector arrays 240 and 340 may be similar except that the detector array 240 requires an opening in its center so that the optical fiber can be in contact with the surface of the Consumable Product 260 and typically the optical window. In FIG. 3A, the optical signal may be collected from the Consumable Product 260 using optical components such as a set of lenses 312 and 313 that project the light from the Consumable Product 260 onto the detector array 340. The fiber 331 is brought in contact with the Consumable Product 260 surface in order to reduce the collection of light directly reflected and backscattered without absorption by the Consumable Product 260. The fiber 331 is similar to the fiber 230 but is positioned parallel to the surface of the Consumable Product 260 to reduce the interference of the fiber 331 on the signal of interest. The light from the fiber 331 is re-directed 90 degrees to the Consumable Product 260 using an angled, reflecting surface or similar optical element so that it falls on the Consumable Product 260 surface in an approximately perpendicular direction. The optical collection efficiency of FIG. 2 may be higher than that of FIG. 3A, but the FIG. 3A system eliminates the need to have an optical window between the detector array 240 and the Consumable Product 260 surface.

Another detection subsystem of the optical engine architecture of FIG. 2 is depicted in FIG. 3B, where the elements in the assembly 270 of FIG. 2 are substituted by the elements in the assembly 371 of FIG. 3B. The differences between these two assemblies lie in the free space illumination component 350 and the detector array 341 which allows edge, corner, or center illumination. A smaller detector array may be used in FIG. 3B as compared to the detector array in FIG. 2. When the detected signal spatial distribution has at least two fold symmetry, the detector array 341 only needs to capture a quarter of the solid volume, i.e. solid angle of π. If the detected signal spatial distribution has four fold symmetry or is isotropic, the detector array 341 only needs to capture an eighth of the solid volume area without loss of data such that an even smaller detector array may be used. The free space, non-contact illumination with optional z direction movable lens in the free space illumination component 350 can focus the light at or below the surface of the Consumable Product 260. The fiber 230 described in FIG. 2 can also be employed with edge, corner or center illumination.

Even though the optical architectures in FIGS. 2, 3A and 3B have a single illumination beam, multiple illumination beams can be employed to optimize signal acquisition with these engines.

Optical architectures for spectral acquisition that do not require an interferometer include systems with a detector array having optical filters and systems with tunable light sources that are substituted for the broadband light sources. Referring now to FIGS. 4 and 4B, a detector array with filters is illustrated from both a top and side view. According to some embodiments, this detector array with optical filters includes a substrate 410, ROIC CMOS array 420, photosensitive sensor array 430, and optical filter array 440, referred to below simply as filter array. Each block of the sensor array that collects light for similar, but not identical, optical paths may have a full array of optical filters for the desired spectral region and resolution. These filter arrays may be repeated for each pseudo identical optical path, providing spectra corresponding to multiple optical paths. Minor differences between optical paths within one full block of filter arrays may be taken into account in data processing the detected signals from the Consumable Product 260.

The individual detector blocks 400 have filter array 440 with optical filters 441, 442, 443, 444 fabricated over photosensitive sensor array 430, thus providing spectral filtering without the use of interferometry, dispersive spectrometry, or tunable light sources. The simplest filter array 440 may be composed of color filters, but such filters have relatively poor spectral resolution because the filter transmission is relatively broad. Interferometric filters, such as Fabry Perot (FP) types, can deliver high spectral resolution defined by filter construction. The simplest FP type filters contain a single cavity, whose gap thickness defines the central wavelength of the transmitted light, and two stacks of multilayers above and below the cavity that are composed of one or more sets of layers of alternating high and low refractive indices. The transmission bandwidth of the filter depends on whether there are multiple repeating structures with multiple cavities. The characteristics of the interferometric transmission filter are strongly dependent on the incident angle, and the spectral resolution can be maintained only when the incident angle range is controlled. The angular range may be controlled by adding a segmented window that contains as many window frames as there are interference filters and detectors. The window frames employed with the filter array 440 should have strong light absorption for light falling on the interferometric filter in a narrow range. The detector array may be configured so that the photosensitive sensor array 430 (or window covering the array that is not shown) is in contact with, or in close proximity to, the Consumable Product 260 surface, followed by the ROIC CMOS array 420 and the substrate 410.

In the contact detector configurations of FIGS. 2, 3B and 4A and 4B, the surface scattering issue may be eliminated. To minimize optical losses of detected signals at a Consumable Product surface- detector (or window) interface, a refractive index matching liquid (such as fluorinated liquid) can optionally be included.

In some embodiments, the detector array with an optical window, but without a filter array, may have a segmented window. A segmented window eliminates the optical cross talk between the sensor elements. Diffusely scattered light has optical rays with varying angles of incidence on the window surface which would allow them to propagate in a waveguiding manner through the window plate. Consequently, the light beam falling on any given window section may refract at the window interface, propagate with multiple reflections into surrounding sensors, and lead to optical cross talk. The reflecting frames in the window structure, as opposed to absorbing frames required with the filter arrays, may confine the light within individual sensors, preserving the light intensity without significant losses and preventing waveguiding propagation.

Figure 5A:
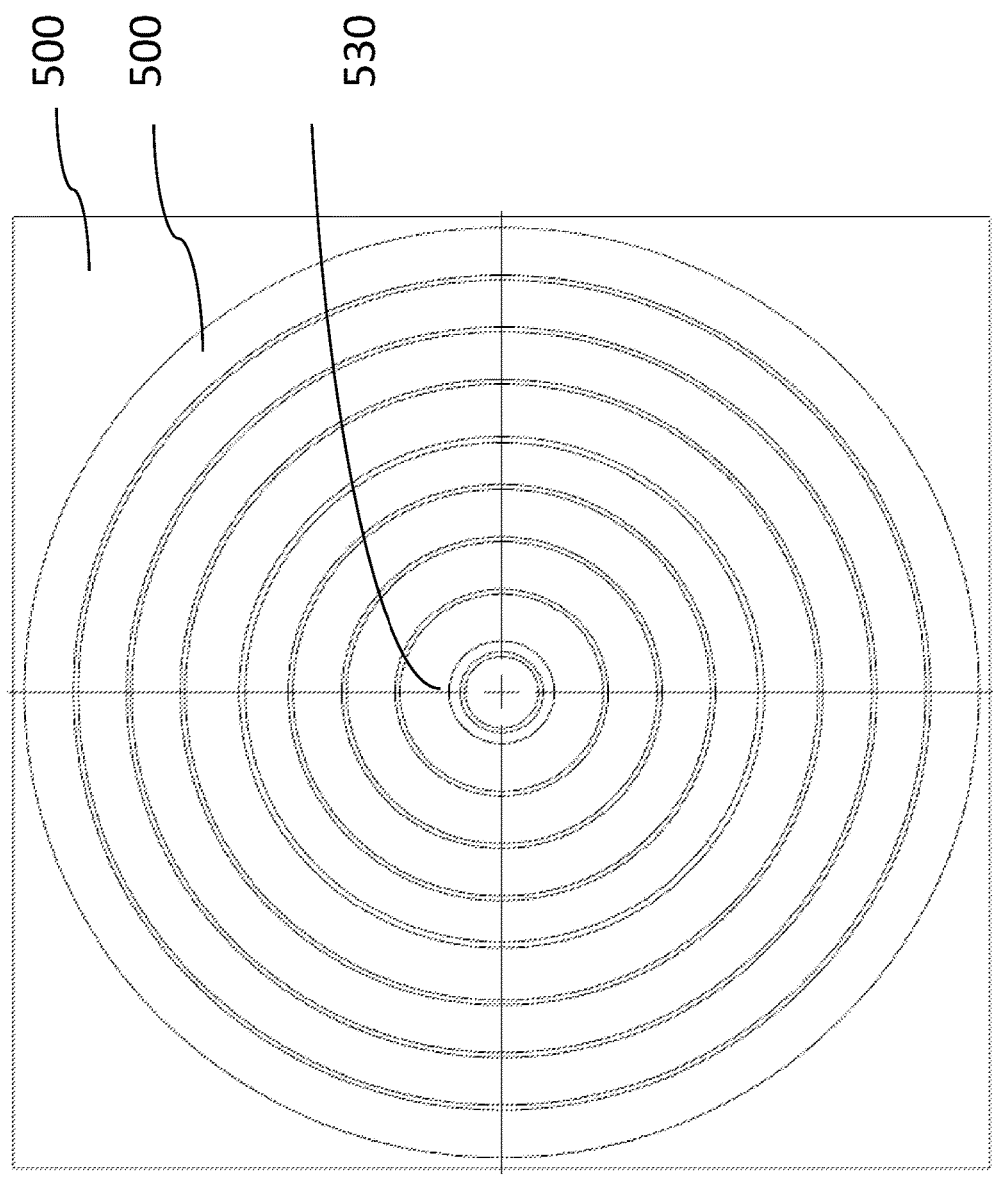
FIGS. 5A-5B show a radial sensor array with central optical fiber illumination and segmented window in top view and side view, respectively, in accordance with some embodiments.

Referring now to FIGS. 5A and B, detector array 500 with central optical fiber illumination 530 and segmented window 570 in accordance with some embodiments is shown from both a top and side view. The detector array 500 contains photosensor array 510, segmented window 570, substrate 540 with or without ROIC CMOS array, and optional spacer 560. Absorbing or reflecting walls 590 are also present to prevent optical cross talk. The photosensor array 510 is separated from the segmented window 570 by the optional spacer 560 for cooled sensors. In such a case, the photosensor array 510 can be at a different temperature than the Consumable Product 260 surface. The space between the photosensor array 510 and the segmented window 570 can be at vacuum or low pressure. If the photosensor array 510 is operated at the same temperature as the Consumable Product 260 surface, then the optional spacer 560 and gap may not be required. The radial detector array can have an integrated ROIC CMOS array included in the substrate 540 underneath the sensors or separate discrete electronics.

Figure 5B:
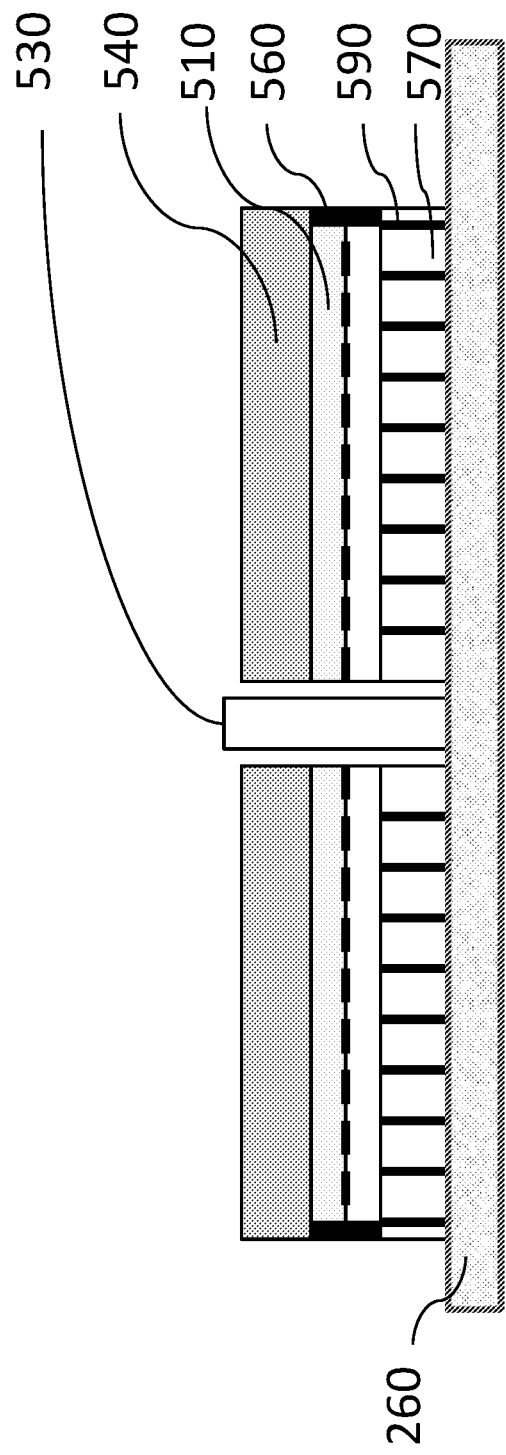

When the number of sensing elements is not too high (say 10 or fewer), as illustrated in FIGS. 5A and 5B with 8 elements, the stacked integration of the ROIC array with the photosensor array 510 may not be required. The amplifiers and digitizers on the separate CMOS chip may be employed instead. The amplifiers and digitizers can be connected to the photosensors with external electrical leads. This optoelectronic configuration does not require stacked sensor-CMOS ROIC integration and is compatible with the optical architecture of FIG. 3A with a non-contact detector. The electrical signal to noise ratio in this side by side photosensor-CMOS integration may not be as high as for a stacked photosensor-CMOS configuration due to higher noise when the sensors are connected with longer electrical leads to external electronic circuits.

The fabrication of these optical engine components is conventional, except for the fabrication of the segmented window with frames and interferometric filter arrays described below. To fabricate a segmented window with frames, the first process relies on coating glass fibers with reflecting material, assembling the glass fibers into large bundles, fusing the fibers together and optionally filling the space between the fibers. Subsequently, the fused fiber bundles are cut into large plates, forming the segmented windows. The second process starts with capillary assembly. Capillaries are assembled into a large bundle and subsequently fused together. Next, the fused bundle is sliced into wafer plates that are coated on the inner walls of the capillaries with light absorbing material. The third fabrication process starts with lithographic patterning of the wafer plate. The deep reactive etching or sandblasting creates openings in the window plate where there is no photoresist coverage. Subsequently, the inner walls are coated with suitable light reflecting or light absorbing material. Alternatively, the frame structure can be formed by injection molding or ultrasonic machining using a patterned plate. The diffractive or refractive lens structures can be added on the entry side of the plate to adjust the acceptance angle of light into the window.

Interferometric filter arrays with narrow spectral transmission may be fabricated by micromachining techniques. When the spectral region of interest is not too wide, only the cavity dimensions have to be strictly controlled for individual filters. The quarter wave layers of alternating high and low refractive indices that form the mirrors surrounding the cavity can be of the same thickness for different filter elements. For interferometric filter arrays with very wide spectral ranges, quarter wave layers require optimized thicknesses. The pattern of variable thickness of cavities or mirror stacks may be produced lithographically with or without photomasks. After depositing a layer patterned with variable thicknesses, one option may use gray scale lithography to define the desired pattern of elements with variable thickness during the subsequent etching step. Another option may be to selectively etch the pattern using photoinduced chemical etching or chemical ion beam etching or electron beam controlled etching.

The materials used in fabricating interferometric filter arrays may be silicon dioxide $SiO_2$ for low refractive index material and tantalum pentoxide $Ta_2O_5$ for high refractive index material. The cavity material can be either high or low refractive index material. Other materials with high refractive indices such as hafnium oxide $HfO_2$ or zirconium oxide $ZrO_2$ and low refractive indices such as magnesium fluoride MgF can also be used.

The photosensors with interferometric filter arrays range from 10,000 to 100,000 elements, with pixel dimensions in the 10 um range and overall chip dimensions of 1000 to 3000 um. Relatively small arrays (3×3 to 8×8) with pixel dimensions of hundreds of microns may also be viable, resulting in sensing chip dimensions ranging from 300 um to 1000 um. Even though specific dimensions are included here, the number of sensing elements in the interferometric filter arrays and their dimensions do not have particular limitations. Infrared absorption spectra or Raman vibrational spectra obtained by the optical engines described above can determine not only the presence or absence of nutritional components, such as vitamins, but also their concentrations in the Consumable Products. In combination with Consumable Product's volume measurements, quantitative amounts of nutrients or vitamins may be established. In addition, the presence or absence of contaminants can be ascertained, including their concentrations, thus providing safety information.

Referring now to FIG. 6, a flow diagram in accordance with some embodiments is shown. At step 610, a picture of a Consumable Product may be taken. The picture of the Consumable Product may be of the item to be consumed, the SKU associated with the item to be consumed, a Reference Object, or any combination thereof. At step 620, the Consumable Product is identified using the different image matching methods described above. It is appreciated that if the Consumable Product cannot be identified for various reasons, e.g., lighting, complex background, etc., the user may be provided with feedback to correct those issues, e.g., take a picture of the Consumable Product with a different background, different angle, different magnification, different lighting, etc. The process may repeat until the Consumable Product can be identified.

At step 630, volume associated with the Consumable Product may be determined as outlined above. At step 640, caloric information associated with the Consumable Product based on the determined volume may be determined. Accordingly, at step 650, health data information based on the caloric and nutrition information associated with the Consumable Product may be rendered, e.g., displayed, audio output, printed, etc. According to some embodiments, the rendered information may be complemented with other types of information, e.g., energy spent and duration of activities.

Referring now to FIG. 7A, a method of determining volume associated with a Consumable Product in accordance with some embodiments is shown. It is appreciated that steps 710-750 may be the steps performed for step 630 in FIG. 6. At step 710, the aspect ratio and resolution of a Reference Image may be adjusted, e.g., increased, decreased, etc., based on the aspect ratio and the resolution of the target image. At step 720, edge(s), shape, color and texture associated with the Consumable Product may be determined. At step 730, the detected edge(s), shape, color and texture associated with the Consumable Product may be compared to corresponding characteristics of the Reference Image. Accordingly, at step 740, the Consumable Product may be identified. At step 750, the volume associated with the Consumable Product may be determined as described above.

Figure 8A:
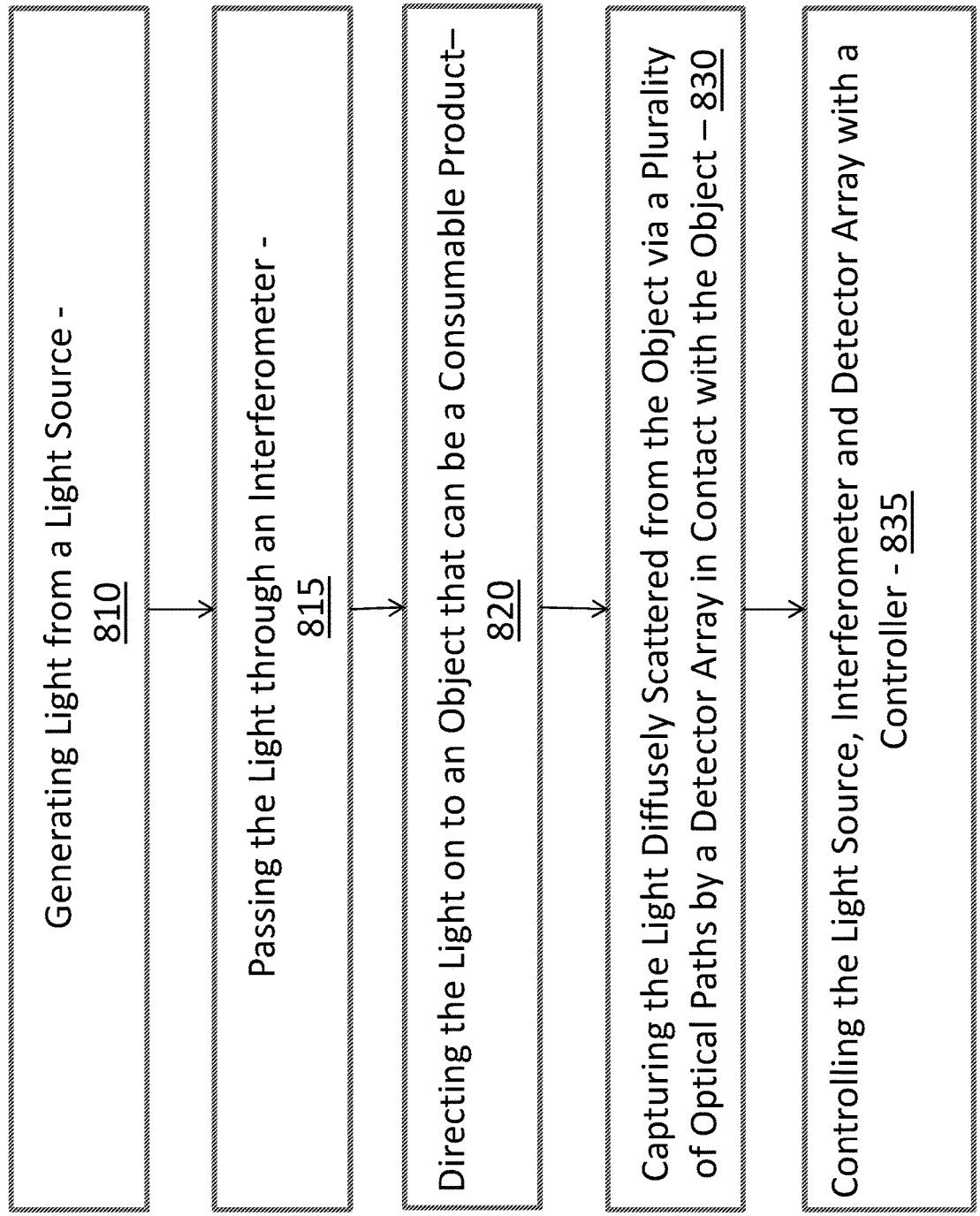
FIG. 8 describes a method of molecular optical fingerprinting based on determining the optical absorption of species of interest.
Figure 8B:
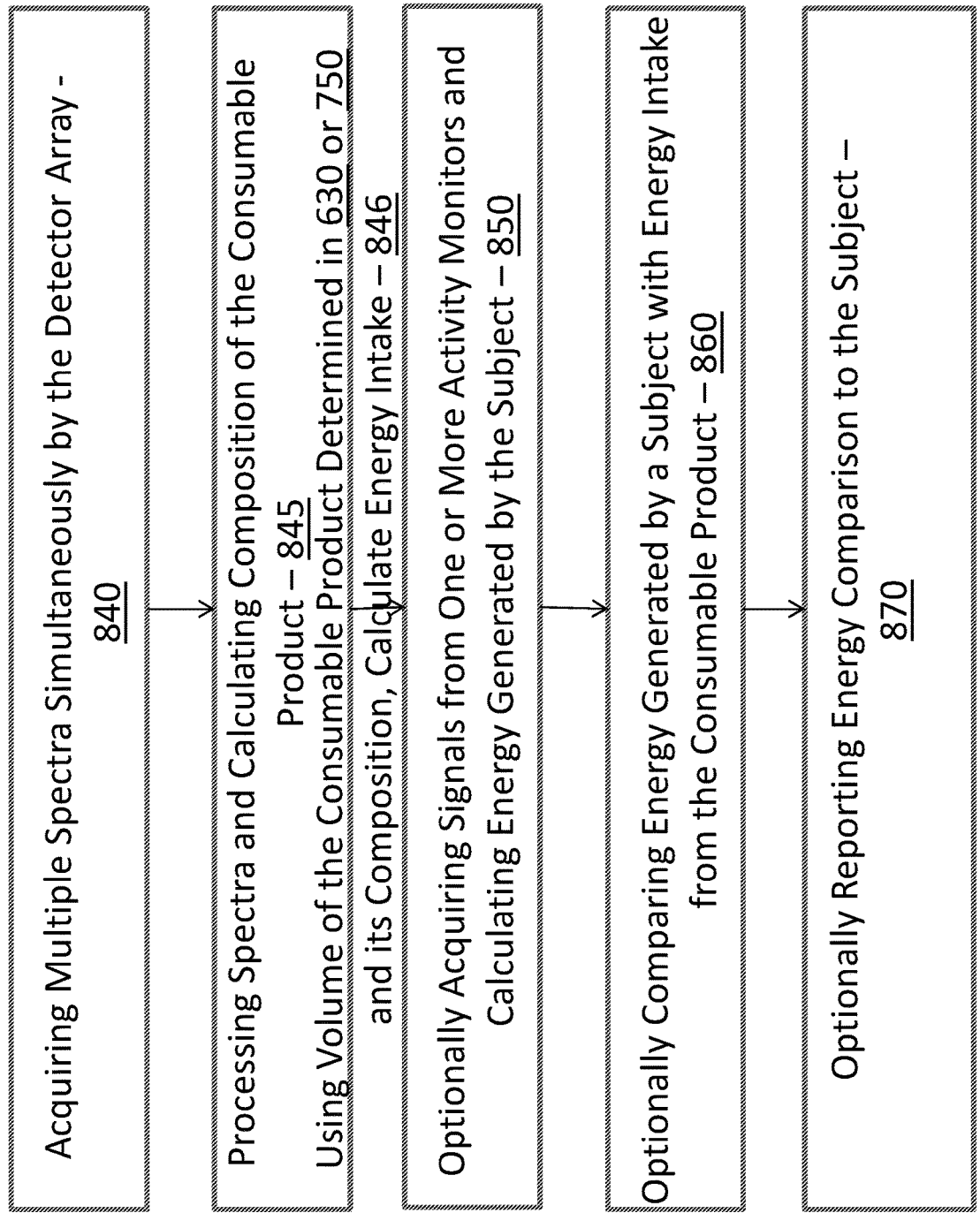

Referring now to FIG. 8, a flow diagram for determining the composition of the Consumable Product in accordance with some embodiments is shown. At step 810, light from a light source is generated. The generated light may be a blackbody light source, LEDs, lasers, tunable lasers or lasers in combination with several phosphorescent materials. At step 820, the generated light is directed on the object, e.g., Consumable Product. It is appreciated that the light may be conducted via various means, e.g., fiber illumination or free space illumination. It is appreciated that the structure of the optical system may be similar to that described in FIGS. 2-5. At step 830, the light diffusely scattered in the interior of the object is detected by a detector array. The proposed architecture reduces the amount of detectable specularly reflected and diffusely scattered light from the surface of the object because the detector array is in contact with or in close proximity to the object.

Accordingly, light absorption can be determined for known, multiple optical paths. As such, at step 850, the composition of the object can be determined. It is appreciated that the determination of the composition may be based on the detected diffusely scattered light from the interior of the object by the detector array.

Figure 9B:
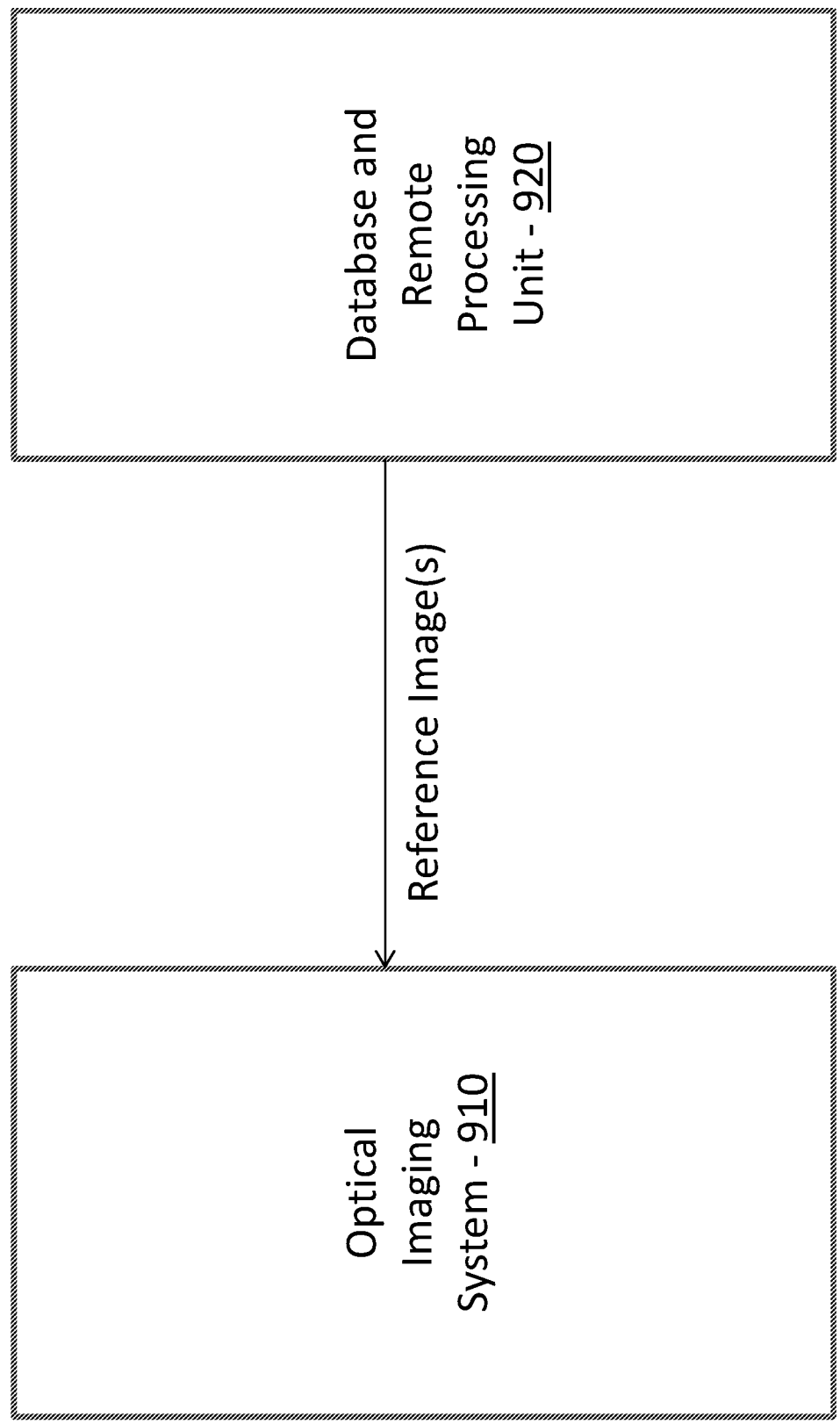

Referring now to FIGS. 9A and 9B, processing of certain information according to some embodiments is shown. More specifically, in FIG. 9A, an optical imaging system 910 in communication with a database and remote processing unit 920 is shown. It is appreciated that the database and remote processing unit 920 may be in the cloud. The database may store various information, e.g., Reference Image(s) of most Consumable Products, as well as their typical compositions, including concentrations. The optical imaging system 910 may take a picture of the Consumable Product to generate the target image 932. The target image 932 may include the Consumable Product, the Reference Object, the SKU, or any combination thereof. The target image 932 may be transmitted from the optical imaging system 910 to the database and the remote processing unit 920 for processing. The remote processing unit 920 may identify the Consumable Product (e.g., orange, apple, meat, type of drink, etc.) and determine its composition (proteins, carbohydrates, fats, sugars, vitamins, minerals, etc.) The remote processing unit 920 may utilize various methods as described in FIGS. 1-8 to make the determination. The database and remote processing unit 920 may transmit the identification of the Consumable Product and the caloric and nutritional information along with the composition of the Consumable Product to the optical imaging system 910 for rendering.

Referring now to FIG. 9B, an embodiment where most of the processing is performed by the optical imaging system is shown. For example, the optical imaging system 910 may receive various information from the database and the remote processing unit 920, such as Reference Image(s) and their composition. The optical imaging system 910 can begin processing the target image once it receives the information from the database and the remote processing unit 920.

In sum, Consumable Product intake with nutritional and other valuable content, including vitamins, etc. and food safety, is provided for improved nutrition, health, wellness, and fitness.

It should be taken into account that other factors in monitoring and tracking the above information may be considered. For example, a user's personal information, including weight, height, sex and age, may be included as part of the health and wellness assessment index calculation. The index may compare energy in, energy out, intake of vitamins and minerals, all relevant nutritional categories of Consumable Products with scaled quantity values, and may contrast them with projected, medically accepted standards. In addition, the index may provide data display, feedback, and recommendations to the user so that any significant positive or negative deviations from projected values can be brought to the user's attention and adjusted accordingly. Specific corrective measures may include, but are not limited to, recommended Consumable Products and supplements and suggestions for more activity or exercise. Accordingly, the optical engine systems described above provide the user with quantitative data on food and liquids, including their volumes, nutritional content, caloric assessment and vitamins and minerals, and contaminants. In combination with the activity monitor, this data can provide the user with comprehensive recommendations for personal nutrition, health, wellness and fitness.

The foregoing description, for purpose of explanation, has been described with reference to specific embodiments. However, the illustrative discussions above are not intended to be exhaustive or to limit the claimed embodiments to the precise forms disclosed. Many modifications and variations are possible in view of the above teachings.

What is claimed is:

1. A device comprising:
    an optical imaging system configured to acquire an image of a consumable product including a reference object;
    storage media containing databases of reference images, compositions, concentrations and energy densities, and storing the image;
    a processor configured to identify the consumable product and further configured to determine the volume of the consumable product using the volume of the reference object, wherein the processor is further configured to use the composition, concentrations and energy densities of the identified reference image, acquired from a communication link to a cloud, to determine the caloric intake of the consumable product;

a rendering component configured to render the caloric intake of the consumable product and provide recommendations to a user; wherein the rendering component is further configured to render the energy spent by the user, activity monitors including accelerometer, gyroscope, pressure sensor and global positioning sensors, wherein the activity monitors are configured to determine the energy spent by the user; and a timer to record the duration of an activity.

2. The device of claim 1, wherein the optical imaging system includes a stereo camera providing three-dimensional images.

3. The device of claim 1, wherein the optical imaging system includes a camera providing two-dimensional images and a processor to determine the third dimension based on: a) the database of reference images or the reference object image, or b) images of the reference object's shadow, or c) images or video of the consumable product taken from at least two different viewing angles.

4. The device of claim 1, wherein the storage media and the processor reside partly in the cloud.

5. The device of claim 1, wherein the consumable product is identified by matching its image, shape, color and texture to an image stored in the database of reference images after the resolution and aspect ratio associated with such image are adjusted to the resolution and aspect ratio of the consumable product's image.

6. The device of claim 1, wherein the image of the consumable product including the reference object with known dimensions allows determination of image magnification and volume of the consumable product.

7. The device of claim 1, wherein the reference object's shadow with known dimensions allows determination of image magnification of the consumable product, removal of the consumable product's shadows and determination of the consumable product's volume.

8. The device of claim 1, wherein the images of the consumable product including the reference object include at least two viewing angles or a video with variable viewing angles.

9. The device of claim 1, wherein the image of the consumable product contains stock keeping unit information of the consumable product.

10. The device of claim 1, wherein the processor is further configured to compare the colors contained in the image of a pH strip to reference colors contained in a database to determine the pH value, and wherein the rendering component reports the pH value of various liquids, including saliva and urine.

11. The device of claim 1, further comprising audio, text or other data input for improved identification of the consumable product.

12. The device of claim 1, wherein the processor is further configured to identify and remove image shadows and illumination differences.

13. The device of claim 1, wherein the processor is further configured to use repeat patterns and learning algorithms for image matching and recognition.

14. The device of claim 1 wherein the rendering component provides recommended actions to the user based on the caloric intake and energy spent and the user's personal information.

15. A method for determining caloric intake from a consumable product and energy spent by a user comprising; acquiring an image of the consumable product including a reference object with an optical imaging system; calculating the magnification of the image using known dimensions of the reference object; determining the volume of the consumable product using the calculated image magnification; identifying the consumable product with a processor configured for image matching and recognition; acquiring the composition, concentrations and energy densities of the identified reference image from a database; calculating the caloric intake of the consumable product using the energy densities of the identified consumable product; acquiring data from activity monitors; determining the energy spent by the user using the data from the activity monitors; and a rendering component configured to render the caloric intake of the consumable product, energy spent by the user, energy balance and nutritional content, and to provide recommendations to the user.

* * * * *